United States Patent [19]
Abe et al.

[11] Patent Number: 5,304,671
[45] Date of Patent: Apr. 19, 1994

[54] METHOD FOR RECOVERY OF ALPHA-L-ASPARTYL-L-PHENYLALANINE METHYL ESTER, L-PHENYLALANINE AND L-ASPARTIC ACID

[75] Inventors: Sou Abe; Shinichi Kishimoto; Tadashi Takemoto; Toshihisa Kato; Satoshi Kumon, all of Kawasaki, Japan

[73] Assignee: Ajinomoto Co., Inc., Tokyo, Japan

[21] Appl. No.: 925,039

[22] Filed: Aug. 5, 1992

[30] Foreign Application Priority Data

Aug. 5, 1991 [JP] Japan ................... 3-195404

[51] Int. Cl.⁵ ........................... C07C 229/34
[52] U.S. Cl. ........................ 560/41; 562/443; 562/554; 562/571
[58] Field of Search ............... 560/41; 562/443, 554, 562/571

[56] References Cited

U.S. PATENT DOCUMENTS

| | | | |
|---|---|---|---|
| 4,348,317 | 9/1982 | Bachman | 560/41 |
| 4,677,220 | 6/1987 | Tou et al. | 560/41 |
| 4,822,907 | 4/1989 | Sugiyama et al. | 560/41 |

Primary Examiner—José G. Dees
Assistant Examiner—Samuel Barts
Attorney, Agent, or Firm—Oblon, Spivak, McClelland, Maier & Neustadt

[57] ABSTRACT

A method for the recovery of α-L-aspartyl-L-phenylalanine methyl ester, L-phenylalanine and L-aspartic acid from the mother liquor obtained by the solid-liquid separation of a suspension of α-L-aspartyl-L-phenylalanine methyl ester crystals is disclosed.

15 Claims, 1 Drawing Sheet

METHOD FOR RECOVERY OF ALPHA-L-ASPARTYL-L-PHENYLALANINE METHYL ESTER, L-PHENYLALANINE AND L-ASPARTIC ACID

BACKGROUND OF THE INVENTION

1. Field of the Invention

The present invention relates to a method for the recovery of α-L-aspartyl-L-phenylalanine methyl ester, L-phenylalanine and L-aspartic acid from dilute solutions containing α-L-aspartyl-L-phenylalanine methyl ester (hereafter abbreviated as α-APM) which comprises recovering α-APM from a mother liquor from which α-APM has already been crystallized out of, and also recovering L-phenylalanine and L-aspartic acid after hydrolysis.

More particularly, the present invention relates to a method for recovery of α-L-aspartyl-L-phenylalanine methyl ester, L-phenylalanine and L-aspartic acid which comprises concentrating part or all of the mother liquor obtained by the solid-liquid separation of a suspension of α-L-aspartyl-L-phenylalanine methyl ester crystals, either taking a part of the resulting concentrate (Solution A) and adding a mineral acid and methanol thereto or mixing Solution A with a solvent comprising mineral acid, methanol, water, and, optionally, α-L-aspartyl-L-phenylalanine methyl ester, to recover α-L-aspartyl-L-phenylalanine methyl ester and/or its acid addition salt analogue (α-L-aspartyl-L-phenylalanine methyl ester acid salt), and hydrolyzing the remaining concentrate and, if desired, the remaining mother liquor with a mineral acid to recover L-phenylalanine or L-phenylalanine and L-aspartic acid.

2. Discussion of the Background

α-APM is a peptide sweetener which exhibits a sweetness about 200 times that of sucrose. Because of its sweetness, extremely high flavor quality and low calorie content, α-APM has been widely used as a dietetic sweetener in recent years. It is expected that world α-APM demand will exceed 10,000 tons/year by 1995.

α-APM has been prepared on an industrial scale according to the following methods: (1) condensing an N-protected aspartic anhydride with L-phenylalanine methyl ester in an organic solvent and removing the protecting group in a conventional manner (U.S. Pat. No. 3,786,039); (2) converting α-L-aspartyl-L-phenylalanine in a mixture of water, methanol and hydrochloric acid into the methyl ester to form α-APM hydrochloride, followed by neutralizing the hydrochloride to give α-APM (Japanese Patent Application Laid-Open No. 53-82752); and (3) condensing an N-protected aspartic acid with phenylalanine methyl ester in the presence of an enzyme followed by removal of the protecting group (Japanese Patent Application Laid-Open No. 55-135595).

In the chemical synthesis described in (1) above, impurities including β-isomers (i.e., β-L-aspartyl-L-phenylalanine methyl ester) are necessarily produced as unwanted by-products. In order to selectively remove these impurities, a method for purification is known which comprises contacting impure α-APM with a hydrohalic acid and performing solid-liquid separation to isolate α-APM as the hydrohalide salt (4).

The most popular method of industrial preparation of α-APM is via the methyl ester hydrochloride obtained after esterification, as shown in (2) above. Further, and as shown in (4) above, the purification of α-APM is often pursued through the hydrohalide. In order to obtain α-APM from its hydrohalide, including the hydrochloride, it is conventional to dissolve or suspend the hydrohalide of α-APM in an aqueous medium followed by the addition of aqueous solutions of sodium carbonate, sodium oxide, sodium hydrogencarbonate or ammonia to carry out the neutralization.

In preparing α-APM on an industrial scale, the mother liquors formed during the course of isolating and purifying α-APM contain, in addition to un-isolated α-APM, compounds associated with its production such as α-L-aspartyl-L-phenylalanine (α-AP), β-L-aspartyl-L-phenylalanine methyl ester (β-APM,), β-L-aspartyl-L-phenylalanine (β-AP), 5-benzyl-3,6-dioxo-2-piperazineacetic acid (DKP), α-L-aspartyl(β-methyl)-L-phenylalanine methyl ester (α-A(M)PM), α-L-aspartyl(β-methyl)-L-phenylalanine (α-A(M)P), N-formyl-α-L-aspartyl-L-phenylalanine methyl ester, and large quantities of inorganic salts due to prior neutralization(s). The type and amount of inorganic salts vary depending upon an alkali used to neutralize the α-APM hydrohalide such as α-APM hydrochloride, etc. Generally, the inorganic salts are NaCl, NH$_4$Cl, KCl, etc.

The recovery of valuable starting materials, particularly the amino acids used as the main raw materials in the production of α-APM, from the mother liquors mentioned above greatly contributes to an overall reduction in the production costs of α-APM. In order to enhance productivity on an industrial scale, it is extremely important to recover these substances. Furthermore, it is advantageous that any recovery process also lead to a reduction in the organic materials present in any waste liquid(s) so a to reduce the overall cost of waste treatment.

The following techniques are known for recovery of α-APM starting materials: (1) hydrolyzing β-APM with an aqueous mineral acid solution and precipitating L-phenylalanine at Ph of 4 to 8, and then precipitating L-aspartic acid at a Ph of 3 to 1 (Japanese Patent Application Laid-Open No. 48-97812), (2) concentrating one or more filtrates, etc. used in the preparation of α-APM, hydrolyzing the concentrate, rendering the concentrate acidic to precipitate the salt of L-phenylalanine, and adjusting Ph of the mother liquor to obtain L-aspartic acid (Japanese Patent Application Laid-open No. 57-130958), and (3) concentrating the mother liquor formed during the course of preparing α-APM below 70° C., hydrolyzing the concentrate to recover L-phenylalanine and L-aspartic acid (Japanese Patent Application Laid-Open No. 63-159355).

SUMMARY OF THE INVENTION

According to the recovery methods described above, unrecovered α-APM and the contaminate by-products contained in mother liquors are hydrolyzed, and L-phenylalanine and L-aspartic acid are recovered. Unfortunately, however, the overall efficiency of such methods is extremely poor: any unrecovered α-APM present is destroyed. Therefore, a method for the recovery of α-APM or its acid salt analogue from mother liquors, without decomposing it into L-phenylalanine and L-aspartic acid, is desired.

In order to solve the foregoing problem, the present inventors have made an extensive investigation into the problem and have developed the present invention which is explained below.

That is, the foregoing problem has been solved by developing a method comprising concentrating part or all of the mother liquor obtained from the solid-liquid separation of a suspension of α-L-aspartyl-L-phenylalanine methyl ester crystals from which no inorganic salt per se has been removed, i.e., the liquor is used "as is" and without desalting: no dissolved materials, including inorganic salts, are removed from the mother liquor (Solution A), and then either adding a mineral acid and methanol to a part of the resulting concentration or mixing a part of the resulting concentration with a solvent comprising of a mineral acid, methanol and water containing, or free of, α-L-aspartyl-L-phenylalanine methyl ester, to recover α-L-aspartyl-L-phenylalanine methyl ester and/or its acid analogue (α-L-aspartyl-L-phenylalanine methyl aster acid salt), and hydrolyzing the remaining Solution A with a mineral acid to recover L-phenylalanine or L-phenylalanine and L-aspartic acid. In this way the unit consumption of L-phenylalanine and L-aspartic acid used per mole of α-APM is reduced, resources can be efficiently utilized, and the amount of organic material in the waste liquid is reduced, resulting in excellent overall efficiency.

Where a "part" of a particular solution is or may be used, part by volume is meant, said part being any non-zero percentage less than 100 percent of the original volume of the initial solution.

It is preferred that the amount of mineral acid and methanol to be mixed with concentrated Solution A (obtained by subjecting a suspension of α-APM crystals to solid-liquid separation and concentrating all or part of the mother liquor) in order to recover α-APM as its acid salt be in a proportion such that the mineral acid is used in at least a 1 to 1 mol/mol ratio of α-APM present in the concentrate, and methanol is used in such an amount so as not to produce the dimethyl ester (α-A(M)PM) from α-APM (not greater than 15 wt % based on the mixture). When the mineral acid is mixed with Solution A, inorganic salts may sometimes be precipitated depending upon composition of the mineral acid and methanol; in this case, the inorganic salts are filtered together with the α-APM acid addition salt and brought into the following step of neutralization and crystallization of α-APM. However, if the inorganic salts are present in such small amounts that they can be removed in the neutralization and crystallization step, the salts are not taken up into the final α-APM product.

Another embodiment for recovering α-APM from Solution A includes, where the main steps for the preparation of α-APM contain a step of crystallization the α-APM acid salt, incorporation of part of Solution A into the crystallization step. In this manner, the amounts of solution components are controlled so as to avoid precipitation of inorganic salts, making the ensuing steps easier. For example, where the acid salt is the hydrochloride, it is preferred that additional Solution A be added to adjust the sodium chloride concentration after crystallization of α-APM hydrochloride to 6 g/dl or less, assuming that the concentration of hydrochloric acid in the solution of α-APM hydrochloride is 3.5 normal and the α-APM hydrochloride solution is cooled to 5° C. after neutralization. The solubility of the α-APM acid salt decreases in the presence of solution-formed inorganic salts because of an effect associated with salting out or "desalting". Accordingly, when the salt concentration is too low after neutralization of the α-APM acid salt solution, the yield of the α-APM acid salt is reduced. It is thus not preferred to lower the salt concentration beyond the necessary level. Furthermore, it is advantageous to have some inorganic chlorides present, thus reducing the amount of hydrogen chloride required for crystallization, as shown in Japanese Patent Application Laid-Open No. 62-16498.

Where large amounts of α-AP are contained in solution, α-AP crystallizes during the crystallization of the α-APM acid salt, resulting in reduction in yield and purity. In this case, therefore, at least 2 mols of methanol per mol of α-AP and hydrochloric acid are added prior to α-APM recovery attempts to convert α-AP into the dimethyl ester (α-A(M)PM). Then α-APM can be recovered as the hydrochloride according to the method of Japanese patent Application Laid-Open No. 59-219258, whereby purity and yield can be improved.

In concentrating part or all of the mother liquor obtained by subjecting a suspension of α-APM crystals to solid-liquid separation, the mother liquor may be concentrated batchwise or continuously; any shape and/or mode of apparatus known in the art may be used. The precipitation of α-APM or any salts as the result of concentration or neutralization steps is to be avoided, however. Therefore, it is preferred that the concentration of α-APM be controlled to obtain solutions whose concentration of α-APM is not greater than the solubility of α-APM at the temperature used for concentration (the solubility of α-APM at 80° C. is 10 g/dl).

The remaining Solution A not used in recovery of α-APM may be concentrated again, if desired. During concentration, the mother liquor obtained after separating the initially obtained α-APM acid salt may be combined with remaining Solution A and the resulting mixture may be concentrated to recover L-phenylalanine and L-aspartic acid after hydrolysis. This embodiment is more efficient than independent recovery.

For hydrolysis of the concentrate, a mineral acid, especially hydrochloric acid, or sulfuric acid is used. It is conventional to perform hydrolysis at a temperature near the boiling point. Hydrolysis over a long period of time is to be avoided in order to prevent racemization. One skilled in the art is familiar with the conditions necessary for hydrolysis.

After hydrolysis, the Ph of the hydrolysate is adjusted to between 4 and 7 using a base such as ammonia, sodium hydroxide, etc. to precipitate L-phenylalanine. Subsequently, the Ph of the mother liquor from which L-phenylalanine has been isolated is further adjusted to 2 to 3 with a mineral acid such as hydrochloric acid, etc. to recover L-aspartic acid. In precipitating L-phenylalanine from the hydrolysate, it is preferred to perform the crystallization under such conditions that the concentration of inorganic salts formed by neutralization reaches nearly the saturation solubility; in this case the solubility of L-phenylalanine becomes small because of salting-out effect which results in a high yield.

The recovered L-phenylalanine and L-aspartic acid are generally re-used to reduce the unit consumption of L-phenylalanine and L-aspartic acid preparing one mole of α-APM. Of course, the recovered L-phenylalanine and L-aspartic acid may also be used as raw materials for synthesis of other chemical substances, without re-cycling them into α-APM.

DETAILED DESCRIPTION OF THE PREFERRED EMBODIMENTS

By recovering α-APM from the mother liquor obtained by separation of an α-APM crystal suspension after neutralization of the α-APM acid salt without decomposing the unrecovered α-APM, efficiency is improved. Furthermore, the unit consumption of L-phenylalanine and L-aspartic acid in producing α-APM is reduced by converting DKP, DKP-OMe, F-APM, APM2, A2PM, β-APM, etc. into L-phenylalanine and L-aspartic acid.

Hereafter the present invention is described by referring to the examples below.

EXAMPLES

Example 1

Run 1

To 197 ml of α-APM solution having the composition shown in Table 1 were added 80 ml of 35% hydrochloric acid and 134 ml of water. Crystallization of α-AP hydrochloride with stirring was carried out at 20° C. for 3 days in a vessel having a volume of 500 ml, and the resulting slurry was sufficiently desupersaturated at 5° C. over a half a day. Filtration gave crystals of α-APM hydrochloride. The thus obtained α-APM hydrochloride crystals were dissolved in 1350 ml of water at 50° C. Thereafter the Ph of this solution was adjusted to 4.8 with 16.4 g/dl of aqueous sodium carbonate to neutralize α-APM hydrochloride. From the obtained α-APM neutralization solution, α-APM was crystallized to give a slurry solution of α-APM crystals. The resulting α-APM crystal slurry solution was subjected to solid-liquid separation and 1510 ml of the mother liquor was concentrated to 222 ml at 70° C. under reduced pressure of 120 torr. 86 ml of the concentrate was used in Run 2.

TABLE 1

|  | mg/ml |  | mg/ml |
|---|---|---|---|
| α-APM | 260.1 | $HCO_2H$ | 20.9 |
| α-APM$_2$ | 49.5 | AcOH | 15.2 |
| α-AP | 36.2 | $HCO_2Me$ | 9.3 |
| α-AMP | 8.0 | AcOMe | 10.7 |
| F-α-APM | 96.7 | MeOH | 80.1 |
| β-APM | 106.5 | $H_2O$ | 391.8 |
| Hcl | 64.1 |  |  |

Run 2

Figure 1:
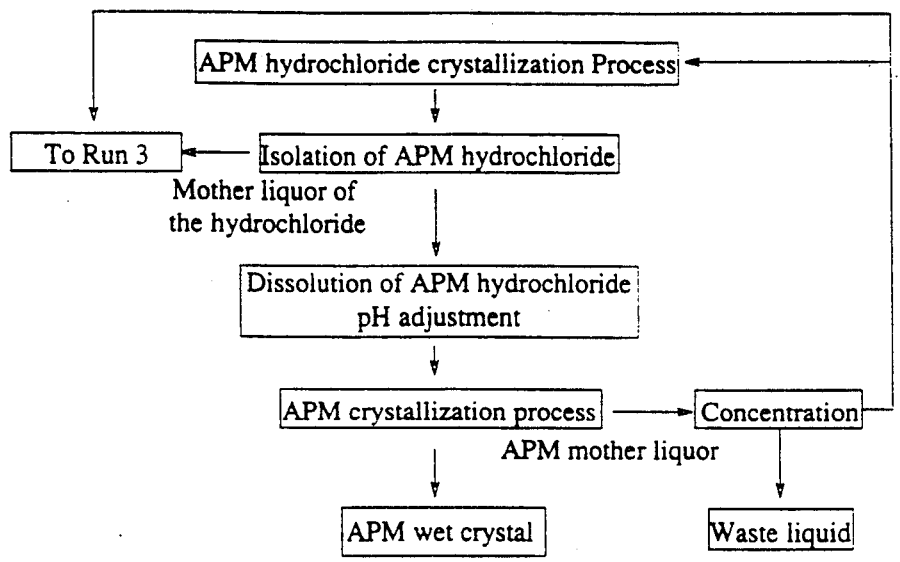
FIGS. 1, 2 and 3 are flow charts describing the runs in Example 1.

Experimental procedures in Run 2 are shown in FIG. 1. To 197 ml of α-APM solution having the composition given in Table 1 were added 80 ml of 35% hydrochloric acid, 48 ml of water and 86 ml of the concentrated α-APM mother liquor obtained in Run 1. Stirring was carried out at 20° C. for 3 days in a vessel having a volume of 500 ml to crystallize α-APM hydrochloride, and the slurry was desupersaturated at 5° C. over a half a day to give crystals of α-APM hydrochloride. During the procedure, no crystals of sodium chloride were crystallized. The α-APM hydrochloride crystals were filtered and the formed mother liquor obtained was later used in Run 3. The thus obtained α-APM hydrochloride crystals were dissolved in 1350 ml of water at 50° C. Thereafter Ph of this solution was adjusted to 4.8 with 16.4 g/dl of sodium carbonate aqueous solution to neutralize α-APM hydrochloride. From the obtained α-APM neutralization solution, α-APM was crystallized to give a slurry solution of α-APM crystals. The resulting α-APM crystal slurry solution was subjected to solid-liquid separation to give 80 g of wet crystals of α-APM. 1510 ml of the mother liquor was concentrated to 112 ml at 70° C. under reduced pressure of 120 torr. 86 ml of this concentrate was circulated to the step of crystallizing α-APM hydrochloride and 26 ml was used in Run 3.

Run 3

Figure 2:
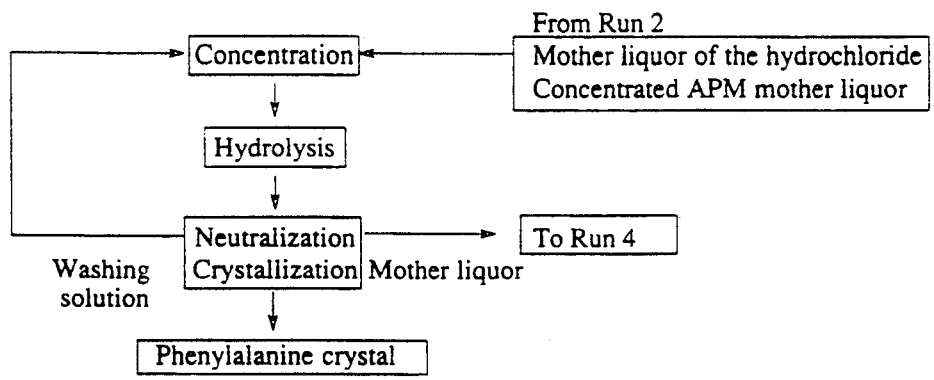

The experimental procedure of Run 3 is shown in FIG. 2. The mother liquor, 292 ml, obtained in Run 2 in which α-APM hydrochloride had been isolated, 26 ml of the concentrated α-APM mother liquor and 41 ml of a washing solution obtained after isolating and washing L-phenylalanine as described below were combined. The mixture was concentrated to 222 ml at 75° C. under reduced pressure of 150 torr. Subsequent to the concentration, this solution was hydrolyzed at 105° C. for 5 hours. Then, the hydrolysate was neutralized to Ph of 5.6 at 85° C. with 68 ml of 48% sodium hydroxide. Cooling to 5° C. gave a slurry solution of L-phenylalanine crystals. From slurry solution, L-phenylalanine was isolated and washed with 44 ml of water to give 34 g of wet crystals of L-phenylalanine. As described above, 41 ml of a washing solution like this one was re-used in the concentration step prior to hydrolysis. After the isolation, 268 ml of the mother liquor was used in Run 4.

Run 4

Figure 3:
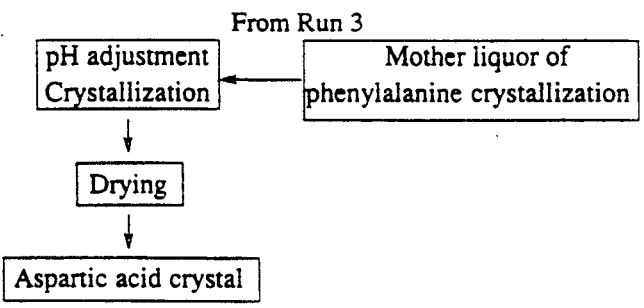

The experimental procedure of Run 4 is shown in FIG. 3. The mother liquor, 268 ml, obtained in Run 3 in which wet crystals of L-phenylalanine had been isolated, was kept at 5° C. and 15 ml of 35% hydrochloric acid Was added thereto to adjust ph to 3.2. The thus prepared slurry solution of aspartic acid crystals was subjected to solid-liquid separation. After isolating aspartic acid, washing with 95 ml of water gave 16 g of crystals of aspartic acid.

Example 2

(Run 1) Preparation of N-formyl-L-aspartic anhydride:

To 671 ml of formic acid, 226 ml of acetic acid and 226 ml of toluene was added 1437 ml of acetic anhydride. After 910 g of L-aspartic acid and 12.8 g of magnesium acetate tetrahydrate were added to the thus prepared solution, the mixture was kept at a temperature of 45° C. and reacted for 3.5 hours with stirring. To the resulting slurry was added 3970 ml of toluene. After ice-cooling for an hour with stirring, the mixture was filtered, while performing suction, to give 917 g of crystalline N-formyl-L-aspartic anhydride.

(Run 2) Preparation of L-phenylalanine methyl ester:

To a mixture of 10.2 liters of methanol and 335 ml of conc. sulfuric acid was added 1050 g of L-phenylalanine. The mixture was stirred at 90° C. for 5 hours to effect esterification. The reaction solution was adjusted with 15% sodium carbonate aqueous solution to a Ph of 7. L-Phenylalanine methyl ester was extracted with toluene to give 10.7 liters of toluene solution of L-phenylalanine methyl ester.

(Run 3) Preparation of α-APM hydrochloride:

With a mixture of the toluene solution of L-phenylalanine methyl ester obtained in Run 2 and 1.4 liter of acetic acid was mixed N-formyl-L-aspartic anhydride obtained in Run 1. The mixture was reacted at 30° C. for 30 minutes. Water was added to the solution and the aqueous phase was separated. Toluene and acetic acid were distilled off from the aqueous solution. To this solution (2.7 liters) containing N-formyl-α-L-aspartyl-L-phenylalanine methyl ester were added 1820 ml of water, methanol and hydrochloric acid (12% of methanol and 32% of hydrochloric acid based on the whole volume of the final solution) to carry out crystallization of α-APM hydrochloride. The obtained α-APM hydrochloride was 1934 g.

(Run 4) Preparation of α-APM and recovery of L-phenylalanine and L-aspartic acid:

The whole amount of α-APM hydrochloride obtained in Run 3 was dissolved in water (23.3 liters). The solution was neutralized with 15% sodium carbonate to adjust Ph to 5. The crystals were subjected to solid-liquid separation to give 1001 g of wet crystals of α-APM. The mother liquor (Solution A) obtained after solid-liquid separation was concentrated to a volume of 1820 ml; 1460 ml of which was stored for circulating to the α-APM hydrochloride crystallization solution in the preparation of α-APM. The remaining 360 ml of Solution A and 4.75 liters of the mother liquor obtained by crystallizing α-APM hydrochloride in Run 3 were combined followed by concentration and hydrolysis with hydrochloric acid. By adjusting the Ph to 5 with sodium hydroxide, 308.7 g of L-phenylalanine was recovered and, subsequently, 312.1 g of L-aspartic acid was recovered from the mother liquor by adjusting the Ph to 3.2. The recovered L-phenylalanine and L-aspartic acid were used as raw materials for the further preparation of α-APM in Run 5. Details of the procedures are similar to those of Example 1.

Run 5

Runs 1-4 were repeated 7 times, producing α-APM, recovering additional α-APM, and then recovering L-phenylalanine and L-aspartic acid. Recovered L-phenylalanine and L-aspartic acid were re-used as raw materials in preparing α-APM. Where either L-phenylalanine or L-aspartic acid were short, fresh L-phenylalanine or L-aspartic acid were replenished as needed. On and after the second repetition, 1090 ml of the concentrated α-APM crystallization mother liquor and 730 ml of water were supplemented upon crystallization of the hydrochloride in Run 2, instead of 1820 ml of water. The unit consumption (weight in kg of fresh raw materials for the preparation of 1 kg of α-APM) of L-phenylalanine and L-aspartic acid were 0.695 and 0.644, respectively. See Table 2.

Example 3

The same procedure as in Runs 1 to 4 of Example 2 were repeated seven times. On and after the second repetition, 1090 ml of the concentrated α-APM crystallization mother liquor and 730 ml of water were supplemented upon crystallization of the hydrochloride in Run 3 of Example 2, instead of 1820 ml of water. The same procedures as in Example 2 were repeated except that 1090 ml out of the mother liquor (Solution A) obtained by solid-liquid separation in Run 4 was stored for circulating to the α-APM hydrochloride crystallization solution in the next run and the remaining 730 ml was used for recovering L-phenylalanine and L-aspartic acid. These same procedures were repeated 7 times. As the result, the unit consumption of L-phenylalanine and L-aspartic acid were 0.706 and 0.657, respectively. See Table 2.

TABLE 2

| | Volume of Solution Circulated (%) | Unit Consumption of Phe | Unit Consumption of Asp |
|---|---|---|---|
| Example 2 | 80 | 0.695 | 0.644 |
| Example 3 | 60 | 0.706 | 0.657 |
| Example 4 | 40 | 0.717 | 0.670 |
| Example 5 | 20 | 0.728 | 0.684 |
| Comparative Example 2 | 0 | 0.739 | 0.697 |

Example 4

The same procedures as in Runs 1 to 4 of Example 2 were repeated seven times. On and after the second repetition, 730 ml of the concentrated α-APM crystallization mother liquor and 1090 ml of water were supplemented upon crystallization of the hydrochloride in Run 3 of Example 2, instead of 1820 ml of water. The same procedures as in Example 2 were repeated except that 730 ml out of the mother liquor (Solution A) obtained by solid-liquid separation in Run 4 was stored for circulating to the α-APM hydrochloride crystallization solution in the next run and the remaining 1090 ml was used for recovering L-phenylalanine and L-aspartic acid. The procedures were repeated 7 times. As the result, the unit consumption of L-phenylalanine and L-aspartic acid were 0.717 and 0.670, respectively. See Table 2.

Example 5

The same procedures as in Runs 1 to 4 of Example 2 were repeated seven times. On and after the second repetition, 360 ml of the concentrated α-APM crystallization mother liquor and 1460 ml of water were supplemented upon crystallization of the hydrochloride in Run 3 of Example 2, instead of 1820 ml of water. The same procedures as in Example 2 were repeated except that 360 ml out of the mother liquor (Solution A) obtained by solid-liquid separation in Run 4 was stored for circulating to the α-APM hydrochloride crystallization solution in the next run and the remaining 1460 ml was used for recovering L-phenylalanine and L-aspartic acid. These procedures were repeated seven times. As a result, the unit consumption of L-phenylalanine and L-aspartic acid was 0.728 and 0.684, respectively. See Table 2.

Example 6

Run 1

To 197 ml of α-APM solution having the composition shown in Table 1 were added 80 ml of 35% hydrochloric acid and 134 ml of water followed by crystallization of α-APM hydrochloride. After crystallization with stirring was carried out at 20° C. for 3 days in a vessel having a volume of 500 ml, the slurry was sufficiently desupersaturated at 5° C. over a half a day. Filtration gave crystals of α-APM hydrochloride. In this case, 290 ml of the mother liquor was obtained and used in Run 3. The thus obtained α-APM hydrochloride crystals were dissolved in 1350 ml of water at 50° C. Thereafter Ph of this solution was adjusted to 4.8 with 16.4 g/dl of sodium carbonate aqueous solution to neutralize α-APM hydrochloride. From the obtained α-APM neutralization solution, α-APM was crystallized to give a suspension of α-APM crystals. The resulting α-APM crystal suspension was subjected to solid-liquid separation and 1520 ml of the mother liquor was concentrated to a volume of 222 ml at 70° C. under reduced pressure of 120 torr. Out of the concentrate, 86 ml was used in Run 2 and 136 ml was used in Run 3. The wet crystals of α-APM obtained was 80 g.

Run 2

To 86 ml of the concentrated α-APM mother liquor obtained in Run 1 were added 34 ml of conc. hydrochloric acid and 8 ml of methanol followed by crystallization of α-APM hydrochloride. After crystallization with stirring was carried out at 20° C. for 3 days in a vessel having a volume of 500 ml, the slurry was sufficiently desupersaturated at 5° C. over a half a day to recover α-APM as crystals of α-APM hydrochloride. During the procedure, no crystals of sodium chloride were crystallized. The α-APM hydrochloride crystals were filtered to give 4.11 g of wet crystals of α-APM hydrochloride.

Run 3

The mother liquor, 290 ml, obtained in Run 2 in which α-APM hydrochloride had been isolated, and 26 ml of the concentrated α-APM mother liquor were combined. The mixture was concentrated to a volume of 222 ml at 75° C. under reduced pressure of 150 torr. Subsequently to the concentration, this solution was hydrolyzed at 105° C. for 5 hours. Then, the hydrolysate was neutralized to pH of 5.6 at 85° C. with 48% sodium hydroxide. Cooling to 5° C. gave a slurry solution of L-phenylalanine crystals. From the slurry L-phenylalanine was isolated and washed with 44 ml of water to give 32 g of wet crystals of L-phenylalanine. After the isolation, 265 ml of the mother liquor was used in Run 4.

Run 4

Experimental procedures of Run 4 are shown in FIG. 3. The mother liquor, 265 ml, obtained in Run 3 in which wet crystals of α-APM had been isolated, was kept at 5° C. and 15 ml of 35% hydrochloric acid was added thereto to adjust pH to 3.2. The thus prepared slurry solution of aspartic acid crystals was subjected to solid-liquid separation. After isolating aspartic acid, washing with 95 ml of water gave 15 g of crystals of aspartic acid.

Comparative Example 1

The same procedures as in Runs 1 to 4 in Example 2 were repeated. Also on and after the second repetition, the same procedures as in Example 2 were performed except that 1820 ml of water was added upon crystallization of the hydrochloride in Run 2. The procedures were repeated 7 times. As the result, the unit consumption of L-phenylalanine and L-aspartic acid were 0.739 and 0.697, respectively. See Table 2.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for the recovery of α-L-aspartyl-L-phenylalanine methyl ester, L-phenylalanine and L-aspartic acid which comprises concentrating all or part of the mother liquor obtained by the solid-liquid separation of a suspension of α-L-aspartyl-L-phenylalanine methyl ester crystals without desalting to provide a concentrate, either adding a mineral acid and methanol to a part of said non-desalted concentrate or mixing a part of said non-desalted concentrate with a solvent comprising a mineral acid, methanol, water and, optionally, α-L-aspartyl-L-phenylalanine methyl ester to precipitate the acid salt, recovering α-L-aspartyl-L-phenylalanine methyl ester as its acid salt, neutralizing said acid salt and recovering α-L-aspartyl-L-phenylalanine methyl ester, hydrolyzing the remaining concentrate with a mineral acid and recovering L-phenylalanine or L-phenylalanine and L-aspartic acid.

2. A method according to claim 1, wherein said part of said concentrate is mixed with sufficient mineral acid and methanol or solvent comprising a mineral acid, methanol, water and, optionally, α-L-aspartyl-L-phenylalanine methyl ester, to form the acid salt and avoid the precipitation of inorganic salts.

3. A method according to claim 1, wherein said suspension of α-L-aspartyl-L-phenylalanine methyl ester crystals is obtained by neutralizing α-L-aspartyl-L-phenylalanine methyl ester acid salt with an alkali.

4. A method according to claim 3, wherein sodium carbonate, sodium hydroxide or ammonia or an organic amine is used as said alkali.

5. A method according to claim 3, wherein the hydrochloride is used as said acid salt.

6. A method according to claim 1, wherein said mother liquor obtained by solid-liquid separation of said suspension of α-L-aspartyl-L-phenylalanine methyl ester crystals comprises α-L-aspartyl-L-phenylalanine methyl ester and at least one of β-L-aspartyl-L-phenylalanine methyl ester, β-L-aspartyl-L-phenylalanine, α-L-aspartyl-L-aspartyl-L-phenylalanine methyl ester, 5-benzyl-3,6-dioxo-2-piperazine acetic acid, 5-benzyl-3,6-dioxo-2-piperazine acetic acid methyl ester, α-L-aspartyl-L-phenylalanine, α-L-aspartyl(β-methyl)-L-phenylalanine methyl ester, α-L-aspartyl(β-methyl)-L-phenylalanine and N-formyl-α-L-aspartyl-L-phenylalanine methyl ester.

7. A method according to claim 1, wherein all or part of said mother liquor is concentrated to a concentration of 2.5 to 10% (w/w) of α-L-aspartyl-L-phenylalanine methyl ester in solution.

8. A method according to claim 1, wherein any remaining mother liquor obtained by solid-liquid separation of said suspension of α-L-aspartyl-L-phenylalanine methyl ester crystals is combined with the remaining concentrate and the resulting mixture is concentrated prior to hydrolysis.

9. A method according to claim 1, wherein said mineral acid used in recovering α-L-aspartyl-L-phenylalanine methyl ester as α-L-aspartyl-L-phenylalanine methyl ester acid salt is hydrochloric acid and the recovered α-L-aspartyl-L-phenylalanine methyl ester acid salt is the hydrochloride.

10. A method according to claim 1, wherein the recovered L-phenylalanine or L-phenylalanine and L-aspartic acid are then re-used as raw material in the preparation of α-L-aspartyl-L-phenylalanine methyl ester.

11. A method according to claim 1, wherein said mineral acid used for hydrolysis is hydrochloric acid.

12. A method according to claim 1 wherein L-phenylalanine is precipitated by adjusting the pH of the remaining concentrate to between 4 to 7 after hydrolysis, and L-aspartic acid is recovered by adjusting the pH of the solution liquor from which L-phenylalanine has been separated to 2 to 3.5.

13. A method according to claim 1 wherein α-L-aspartyl-L-phenylalanine methyl ester, L-phenylalanine and L-aspartic acid are recovered from solutions formed in the preparation of α-L-aspartyl-L-phenylalanine methyl ester using, as raw materials, N-formyl-L-aspartic anhydride and L-phenylalanine methyl ester.

14. A method according to claim 1, wherein said mother liquor obtained by solid-liquid separation of said suspension of alpha-L-aspartyl-L-phenylalanine methyl ester crystals comprises alpha-L-aspartyl-L-phenylalanine methyl ester and at least one of beta-L-aspartyl-L-phenylalanine methyl ester, beta-L-aspartyl-L-phenylalanine, alpha-L-aspartyl-L-aspartyl-L-phenylalanine methyl ester, 5-benzyl-3,6-dioxo-2-piperazine acetic acid, 5-benzyl-3,6-dioxo-2-piperazine acetic acid methyl ester, alpha-L-aspartyl-L-phenylalanine, alpha-L-aspartyl-(beta-methyl)-L-phenylalanine methyl ester, alpha-L-aspartyl-(beta-methyl)-L-phenylalanine and N-formyl-alpha-L-aspartyl-L-phenylalanine methyl ester.

15. A method for the recovery of α-L-aspartyl-L-phenylalanine methyl ester, L-phenylalanine and L-aspartic acid comprising the steps of:
 a) crystallizing the acid salt of α-L-aspartyl-L-phenylalanine methyl ester out of solution followed by filtration to obtain crystals of the acid salt,
 b) suspending the crystals of the acid salt in water followed by neutralization and solid-liquid separation to obtain α-L-aspartyl-L-phenylalanine methyl ester crystals,
 c) concentrating all or part of the mother liquor obtained by the solid-liquid separation of a suspension of α-L-aspartyl-L-phenylalanine methyl ester crystals without desalting to provide a concentrate,
 d) either (1) or (2), or both (1) and (2)
 (1) adding a part of the concentrate obtained in c) to a solution out of which the acid salt of alpha-L-aspartyl-L-phenylalanine methyl ester is to be crystallized,
 (2) i) any one of the steps selected from (i1), (ib) and (ic);
 (ia) adding a mineral acid and methanol to a part of said concentrate obtained in c),
 (ib) mixing a part of said concentrate obtained in c) with a solvent comprising a mineral acid, methanol, water and, optionally, alpha-L-aspartyl-L-phenylalanine methyl ester or its precursor to form the acid salt of alpha-L-aspartyl-L-phenylalanine methyl ester and
 (ic) adding a mineral acid and methanol to a part of said concentrate obtained in c) and then mixing the added concentrate with the solvent in (ib),
 ii) recovering alpha-aspartyl-L-phenylalanine methyl ester as its acid salt from the solution obtained in i), and
 iii) neutralizing said acid salt obtained in ii) and recovering alpha-L-aspartyl-L-phenylalanine methyl ester,
 e) (1) hydrolyzing the remaining concentrate obtained in c) with a mineral acid, and (2) recovering L-phenylalanine or L-phenylalanine and L-aspartic acid from the solution obtained in (1), and
 f) repeating the above steps at least once.

* * * * *